US010188488B2

(12) United States Patent
Montero et al.

(10) Patent No.: US 10,188,488 B2
(45) Date of Patent: Jan. 29, 2019

(54) SCREWLESS DENTAL IMPLANT CONNECTION

(71) Applicant: BIOMET 3I, LLC, Palm Beach Gardens, FL (US)

(72) Inventors: Miguel G Montero, West Palm Beach, FL (US); Zachary B Suttin, West Palm Beach, FL (US); David Rebollar, Boynton Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 15/172,914

(22) Filed: Jun. 3, 2016

(65) Prior Publication Data
US 2016/0354183 A1 Dec. 8, 2016

Related U.S. Application Data

(60) Provisional application No. 62/172,363, filed on Jun. 8, 2015.

(51) Int. Cl.
A61C 8/00 (2006.01)
(52) U.S. Cl.
CPC .......... *A61C 8/0089* (2013.01); *A61C 8/0001* (2013.01); *A61C 8/005* (2013.01);
(Continued)
(58) Field of Classification Search
CPC ..... A61C 8/005; A61C 8/0063; A61C 8/0065; A61C 8/006; A61C 8/0066; A61C 8/0074;
(Continued)

(56) References Cited

U.S. PATENT DOCUMENTS 5,782,918 A * 7/1998 Klardie ................. A61C 8/005
433/172
2004/0191727 A1* 9/2004 Shelemay ............ A61C 8/0012
433/173
(Continued)

FOREIGN PATENT DOCUMENTS

CN 102283714 B 10/2013
DE 20303653 U1 * 4/2004 ........... A61C 8/0022
(Continued)

OTHER PUBLICATIONS

"International Application Serial No. PCT/US2016/035763, International Search Report dated Aug. 4, 2016", 3 pgs.
(Continued)

Primary Examiner — Nicholas Lucchesi
Assistant Examiner — Shannel Wright
(74) Attorney, Agent, or Firm — Schwegman Lundberg & Woessner, P.A.

(57) ABSTRACT

A dental restoration system is disclosed. A dental restoration system includes an implant, retention component, dental component and driver tool. The retention component is seatable in a retention chamber of the implant. The retention component includes a driver section for interfacing with a driving head of the driver tool and a dental component engagement section with a threaded surface. The dental component includes a retention component interface surface with threads. The dental component engages the retention component via the threaded surface interlocking with the threads of the retention component interface surface when the dental component is inserted in the implant. The driver tool is used to rotate the retention component to engage the dental component apically. The retention component contacts the retention component wall and the dental component (Continued)

contacts an annular shoulder of the implant when the dental component is fully attached to the implant.

14 Claims, 12 Drawing Sheets

(52) U.S. Cl.
CPC .......... *A61C 8/0013* (2013.01); *A61C 8/0063* (2013.01); *A61C 8/0065* (2013.01); *A61C 8/0066* (2013.01); *A61C 8/0074* (2013.01); *A61C 8/006* (2013.01); *A61C 8/0069* (2013.01)

(58) Field of Classification Search
CPC ... A61C 8/0075; A61C 8/0069; A61C 8/0013; A61C 8/0062; A61C 8/0089
See application file for complete search history.

(56) References Cited

U.S. PATENT DOCUMENTS

| | | | |
|---|---|---|---|
| 2008/0032263 A1* | 2/2008 | Bondar | A61C 8/0001 433/173 |
| 2008/0182227 A1* | 7/2008 | Wolf | A61C 8/005 433/174 |
| 2013/0196290 A1* | 8/2013 | Herrington | A61C 8/006 433/173 |
| 2013/0295521 A1* | 11/2013 | Olsson | A61C 8/0066 433/173 |
| 2015/0140508 A1* | 5/2015 | Nike | A61C 8/0065 433/172 |
| 2015/0147724 A1* | 5/2015 | Staudenmann | A61C 8/0059 433/201.1 |

FOREIGN PATENT DOCUMENTS

| | | | | |
|---|---|---|---|---|
| DE | 20303653 U1 | 4/2004 | | |
| EP | 0323823 A2 | 7/1989 | | |
| WO | WO-2014185264 A1 | 11/2014 | | |
| WO | WO 2014195955 A1 * | 12/2014 | | A61C 8/0001 |

OTHER PUBLICATIONS

"International Application Serial No. PCT/US2016/035763, Written Opinion dated Aug. 4, 2016", 6 pgs.

"European Application Serial No. 16728574.1, Response filed Aug. 17, 2018 to Office Action dated Feb. 9, 2018", 8 pgs.

* cited by examiner

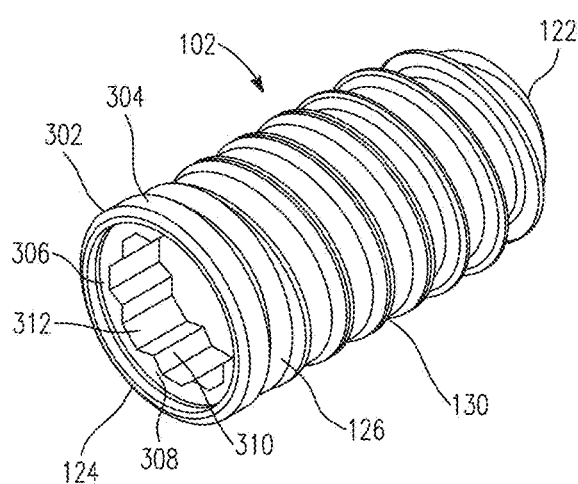
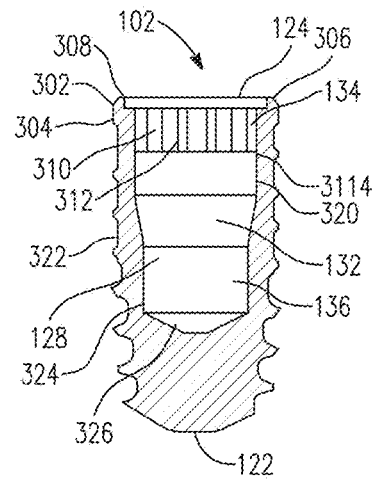
FIG. 3A    FIG. 3B
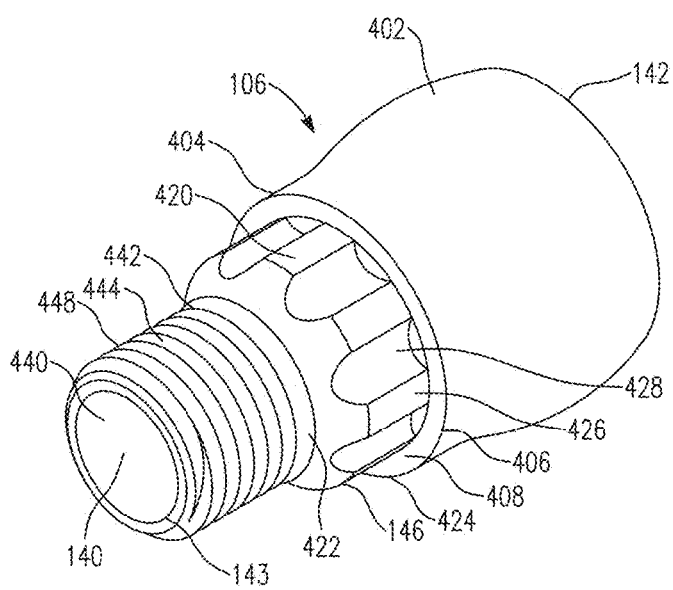
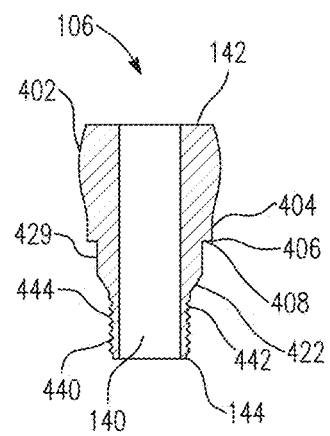
FIG. 4A    FIG. 4B

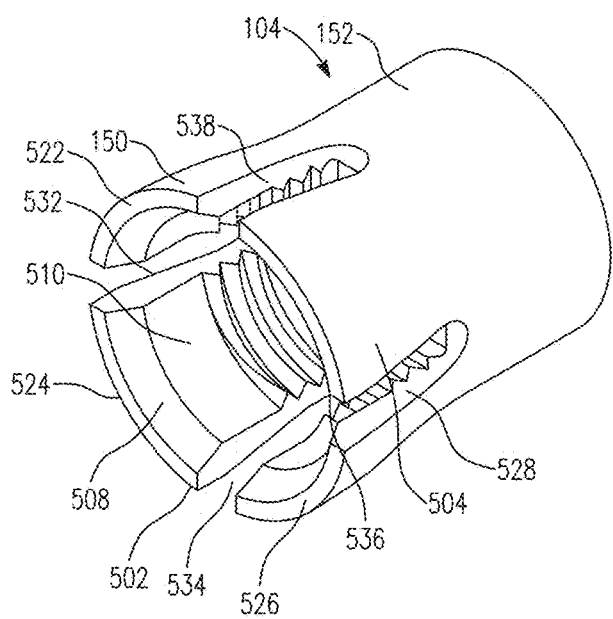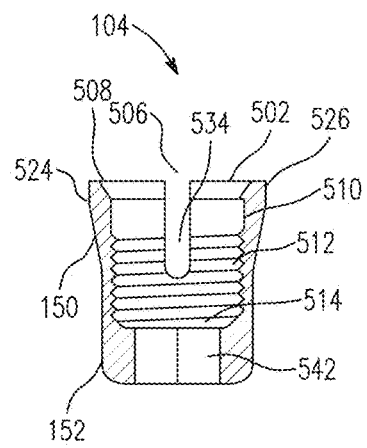
FIG. 5A
FIG. 5B

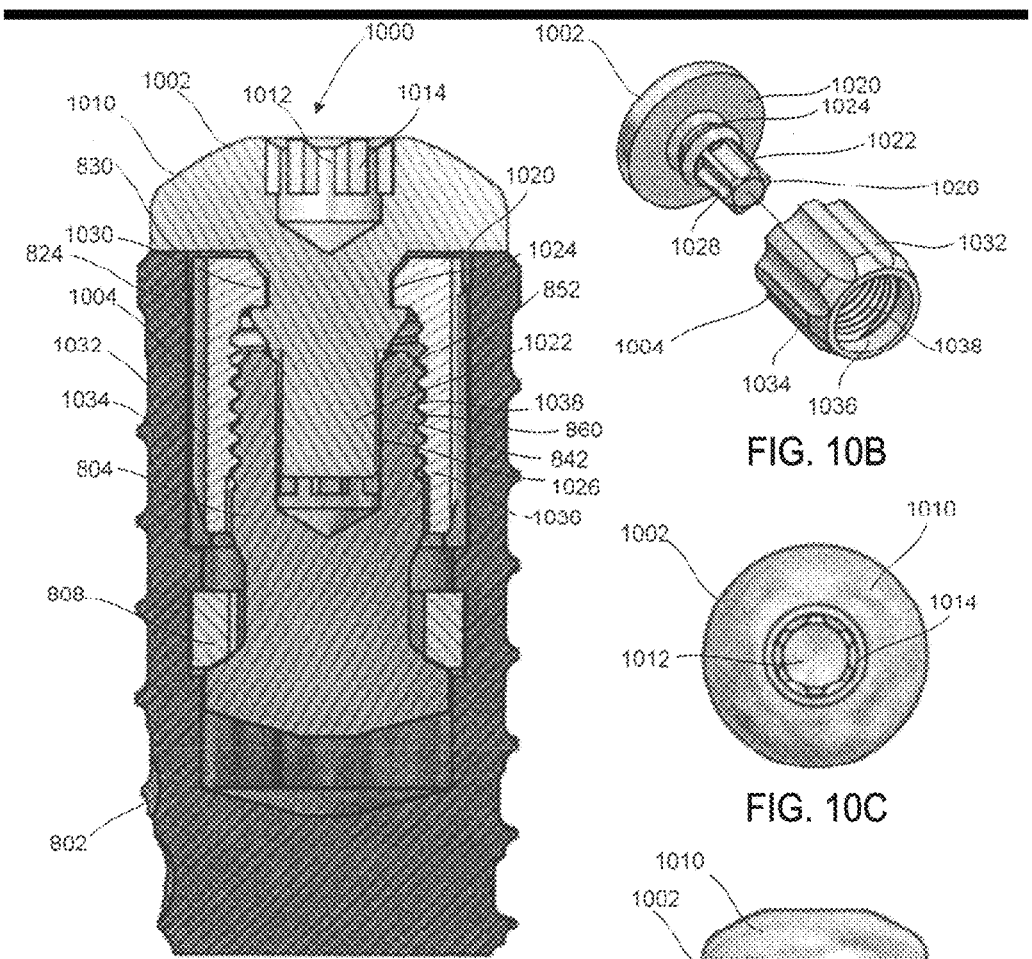
FIG. 10A
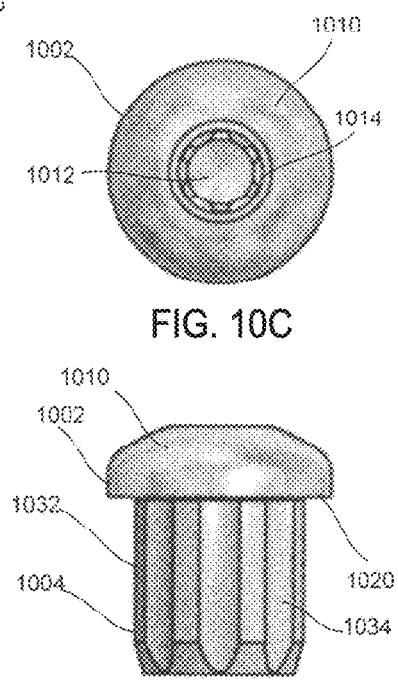
FIG. 10B
FIG. 10C
FIG. 10D

SCREWLESS DENTAL IMPLANT CONNECTION

CLAIM OF PRIORITY

This application claims the benefit of U.S. Provisional Patent Application Ser. No. 62/172,363, filed on Jun. 8, 2015, the benefit of priority of which is claimed hereby, and which is incorporated by reference herein in its entirety.

TECHNICAL FIELD

This disclosure relates to dental implants and more specifically to a screwless connection mechanism for the attachment of a dental implant and a dental component.

BACKGROUND

A well-known procedure is the dental restoration of a partially or wholly edentulous patient with artificial dentition. Typically, a dental implant is seated into the bone of a patient's jaw. The dental implant includes a socket, e.g., a bore, which is accessible through the overlying or surrounding gum tissue for receiving and supporting one or more attachments or components which, in turn, are useful to fabricate and support prosthodontic restorations. The dental implant generally includes a threaded bore to receive a retaining screw for holding mating components therein. Dental implant procedures may use a variety of implanting modalities, for example, blade, threaded implant, or smooth push-in implant.

Single tooth restorations present the unique requirement that the prosthesis must be supported non-rotationally when engaged with the implant. Often times this is achieved through non-rotational support of the underlying abutment. When a prepared natural tooth is the underlying abutment, this requirement is met in the normal course of preparing the abutment with a non-circular cross-section. Likewise, when the underlying abutment is a post fitted onto an implant, this requirement is met by preparing the post with a non-circular cross-section. This latter scenario may be more complicated due to the added connection between the implant and the abutment.

While numerous design iterations have been marketed, overall there have been three generations of the implant-abutment interface within these assemblies: an external hex implant, an internal connection implant, and a vertical connection assembly. The external hexagonal implant design has a hexagonal shape (or another anti-rotation feature) protruding out of the implant and the corresponding prosthesis has a female hexagonal receptacle. There is a surface below the hexagonal protrusion on which the abutment is seated. The hexagonal protrusion acts to constrain the abutment from rotating around the longitudinal axis as well as preventing movement on the plane coincident with the implant seating surface. A screw is introduced and rotated to attach the abutment and the implant. The screw is essentially the sole component resisting bending forces.

Unfortunately, screws are a separate component that must be installed in the implant in addition to the abutment during oral surgery. Screws are small and difficult to deliver into a patient. The size of the screw makes it difficult to hold when inserting the screw into the implant and abutment and runs the risk of being ingested, or even worse, aspirated, if the screw is dropped. Further, a normal screw has a head that sits above the seating surface of the implant. The head limits the degree of angle adjustment of the abutment because the abutment screw head breaks out from the body once a certain angle is achieved, depending on the physical characteristics of the screw (i.e., screw head height and diameter), the location of the screw head, and the angle of the abutment. In order to accommodate a screw (or at least a diameter equivalent to the screw head diameter), the access hole in the abutment must be sized to accept the largest diameter of the screw, and this can often be relative large (compared to the outer diameter of the abutment. This can weaken the structural stability of the abutment, as well as potentially detract from the ultimate aesthetics of the provisional and/or final restoration(s)

Thus, there is a need for a retention component between a dental implant and a mating component such as an abutment that allows the attachment of the implant and the abutment without using a conventional mounting screw. There is a further need for a retention component that is pre-seated in an implant thereby preventing the mishandling of a screw within the oral cavity during oral surgery. There is a further need for an interface between a dental implant and abutment that creates a seal between the two components, thereby preventing and potentially promoting bacterial exchange between the oral cavity and the internal aspect of the implant. There is a further need for an interface between a dental implant and an abutment that allows design flexibility of a restoration having the possibility of an extremely short and/or highly angled restoration without sacrificing strength and/or aesthetics of the restoration.

BRIEF SUMMARY

An example of the present disclosure is a dental restoration system including an implant having a tip, a cylindrical body, and an open end having an annular shoulder. The cylindrical body includes a retention component chamber having a retention component wall. The system includes a retention component seated in the retention chamber of the implant. The retention component including a driver section for interfacing with a driving head of a driver tool and a dental component engagement section with a threaded surface. A dental component includes a retention component interface surface with threads and a bore therethrough. A driver tool includes a driving head. The dental component engages the retention component via the threaded surface interlocking with the threads of the retention component interface surface when the dental component is inserted in the implant. The driving head of the driver tool engages the driver section of the retention component to allow rotation of the retention component via the driver tool to engage the dental component apically. The retention component contacts the retention component wall and the dental component contacts the annular shoulder of the open end of the implant when the dental component is fully attached to the implant.

Another example is a method of connecting a mating component to an implant via a retention component. The implant includes a tip, a cylindrical body, and an open end having an annular shoulder. The cylindrical body includes a retention component chamber having a retention component wall. The retention component includes a driver section for interfacing with a driving head of a driver tool and a dental component engagement section with a threaded surface. The method includes inserting the retention component into the implant where the retention component is at least partially contained in the retention component chamber. The retention component and the implant are inserted into a subject. The mating component is inserted into the implant. The mating component is permitted to interface with the retention component via a threaded connector. The retention component is rotated to join the mating component apically. The mating component is joined with the implant by contacting the retention component against a retention wall and the mating component in contact with the annular shoulder.

Another example is a dental system including a dental implant having an internal bore and a rotatable threaded retention component located within the internal bore. The system also includes an abutment including a lower threaded stem engaging the rotatable threaded retention component. The abutment is pulled into a final engagement position on the implant in response to the rotation of the rotatable threaded retention component.

Another example is a dental implant assembly including an implant having an internal bore extending inwardly from one end of the implant. A rotatable threaded retention component is located within the internal bore. The rotatable threaded retention component has a member that is held captive within the internal bore of the implant and a threaded shank facing upwardly away from a bottom of the internal bore for engaging a corresponding threaded section of a component to be mated to the implant.

Another example is a method of connecting an implant to an abutment. The method includes inserting a lower threaded stem of the abutment into an internal bore of the implant until the lower threaded stem engages a rotatable threaded component within the internal bore the implant. The rotatable threaded component is rotated within the implant to pull the abutment into a final engagement position relative to the implant.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 3A is a perspective view of the dental implant in FIG. 1;

FIG. 3B is a cross-section view of the dental implant in FIG. 1;

FIG. 4A is a close-up perspective view of the mating component in FIG. 1;

FIG. 4B is a cross-section view of the mating component in FIG. 1;

FIG. 5A is a close-up perspective view of the retention component in FIG. 1;

FIG. 5B is a cross-section view of the retention component in FIG. 1;

FIG. 10A is a cross-section view of the assembly of a cover screw dental component assembled with the implant and retention component shown in FIG. 8A-8C;

FIG. 10B is a perspective, exploded view of the components of the cover screw dental component in FIG. 10A;

FIG. 10C is a top view of the cover screw dental component in FIG. 10A

FIG. 10D is a side view of the cover screw dental component in FIG. 10A;

Figure 1:
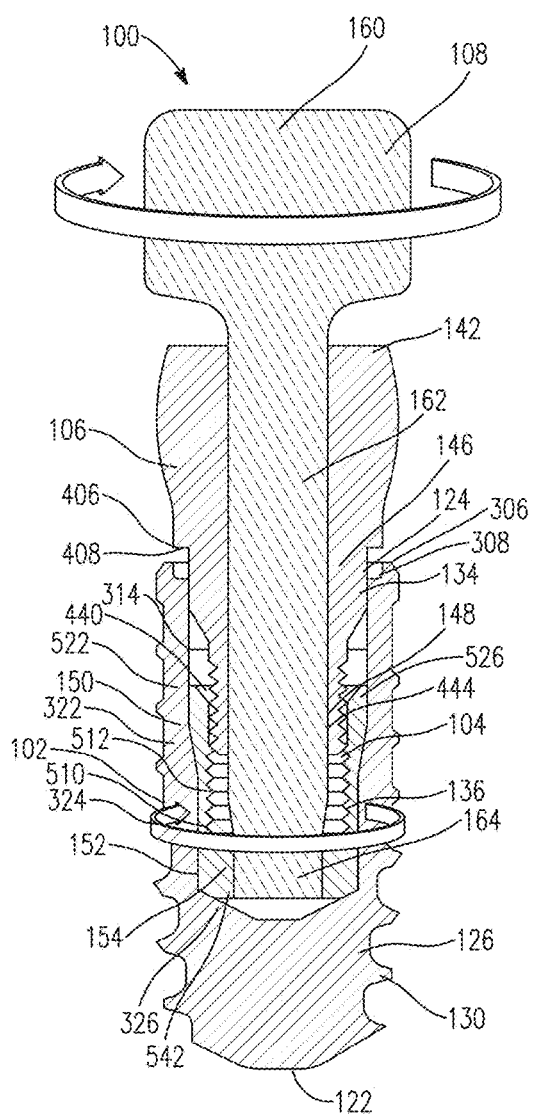
FIG. 1 is a cross-section view of a dental assembly including an implant and a mating component with a retention component being driven via a driver tool.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1 is an exploded perspective view of an implant and mating component interface assembly 100. The interface assembly 100 includes an implant 102, a retention component 104, and a dental mating component 106 that in this example is an abutment. As will be explained below, the retention component 104 is inserted into the implant 102 prior to the insertion of the implant 102 into a patient. The combination of the implant 102 and the retention component 104 are therefore considered an implant assembly. Other mating components may include abutments, impression copings, cover screws, monolithic prostheses, etc. The mating component may also be an attachment member, which when scanned provides data about the implant 102. Such an attachment member conveys information about the implant (i.e., location, orientation, type, etc.) and/or the surrounding conditions (i.e., subgingival tissue contours, etc.). Such an attachment member may be one piece or two pieces. The attachment member may be left in the mouth during healing or it may be attached for a short period of time sufficient to acquire the data.

A driver 108 is shown in FIG. 1 to facilitate the attachment of the mating component 106 with the implant 102. The components shown in FIG. 1 are used in dental restorative processes. As is known, the implant 102 is inserted into the bone of a patient's jaw after a suitable osteotomy is created in the bone. An implant driver tool is used to rotate the implant 102 into the osteotomy and therefore position it in the bone. The dental mating component 106 in this example may be a standard prosthetic part or customized to replace the patient's tooth in this example and is attached to the implant 102 after the implant 102 is seated in the bone. After the dental component 106 is inserted into the implant 102, the dental component 106 is fixed to the implant 102 by using the driver tool 108. As will be explained below, the interface between the implant 102 and the abutment 106 includes the retention component 104 that keeps the implant 102 and abutment 106 joined and properly aligned. This interface provides both controlled vertical location and rotational alignment of the abutment 106 relative to the implant 102. The retention component 104 enforces and maintains this control once the connection between the implant 102 and the abutment 106 is established.

As shown in FIG. 1 and FIGS. 3A-3B, the dental implant 102 has a roughly cylindrical body 120 that includes a closed end 122 and an opposite open end 124. The cylindrical body 120 includes an exterior surface 126 and an interior surface 128. The exterior surface 126 has a series of threads 130 that hold the implant 102 into the bone. The implant 102 includes an interior bore 132 that includes the interior surface 128. The interior bore 132 includes an anti-rotation section 134 and a retention component section 136.

As shown in FIGS. 3A-3B, the open end 124 includes the anti-rotation section 134. The anti-rotation section 134 includes an annular ring 302 defining an exterior surface 304. The annular ring 304 has an annular interior shoulder 306 that includes an annular stop surface 308. The annular stop surface 308 is substantially horizontal and allows the dental component 106 to be seated on a known and repeatable planar surface and creates a seal based on the contact between the stop surface 308 and a matching surface on the mating component 106 as will be explained below.

The anti-rotation section 134 includes a set of circular ridges 310 and grooves 312 that mate with corresponding surfaces on the dental component 106 to prevent rotational motion when the dental component 106 is inserted into the dental implant 102. The ridges 310 and grooves 312 partly create the annular stop surface 308. The opposite end of the ridges 310 and grooves 312 also define a retention stop surface 314 that defines the retention component section 136. The retention component section 136 includes a top section 320 having a first diameter. The top section 320 is defined on one end by the retention stop surface 314. The opposite end of the top section 320 is connected to a conical middle section 322. The conical middle section 322 is connected to a bottom section 324 that has a second diameter that is smaller than the first diameter of the top section 320. The bottom section 324 is bounded by an interior bottom end 326. Of course different types of anti-rotation arrangements such as dual anti-rotation sections may be used.

Figure 2:
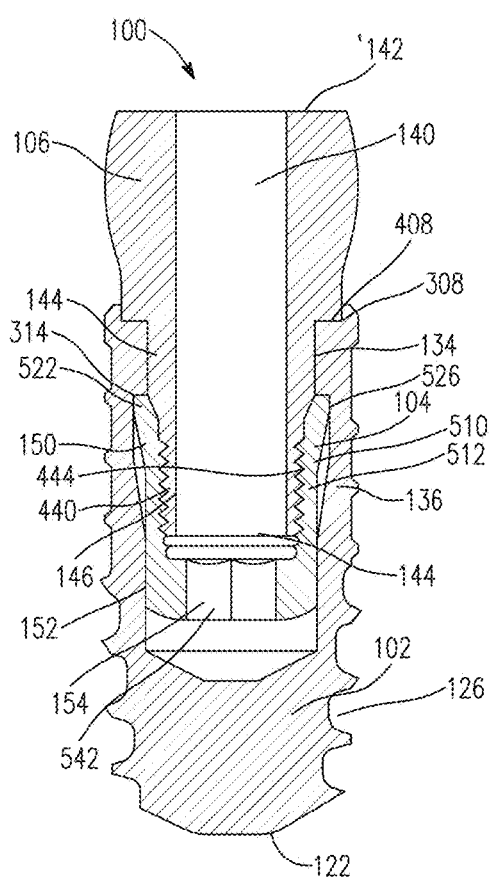
FIG. 2 is a cross-section view of the interface assembly between the implant and the mating component with the retention component in FIG. 1 after the activation (rotation) of the retention component within the implant.

FIG. 1 and FIGS. 4A-4B show the mating component 106. The mating component 106 includes an access hole 140 that extends from a top surface 142 and a bottom end surface 144. The mating component 106 includes a middle anti-rotational section 146 and a bottom retention engagement section 148. As shown in FIG. 1, the mating component 106 is inserted in the interior bore 132 of the implant 102. The middle anti-rotational section 146 engages the anti-rotational section 134 of the implant 102 while the bottom retention engagement section 148 engages the retention component section 136. As shown in FIG. 2, the retention component 104 moves up to eventually contact the retention stop surface 314 when it is rotated by the driver tool 108 in FIG. 1 and locks the mating component 106 with the implant 102.

The top surface 142 of the mating component 106 includes a component head 402 that may be an abutment in this example. The component head 402 in this example is a one piece abutment and includes a bottom cylindrical section 404 that includes a bottom rim 406 that has a planar stop surface 408. The diameter of the bottom cylindrical section 404 is the same diameter of the annular interior shoulder 306 of the implant 102 in FIGS. 3A-3B. The planar stop surface 408 contacts the annular stop surface 308 and creates a seal between the mating component 106 and the implant 102 from joining the two stop surfaces 308 and 408 and the preload generated between the retention component 104 and the mating component 106 as shown in FIG. 2. The two planar stop surfaces 308 and 408 have the additional benefit of establishing a common datum plane, which is utilized throughout the entire restorative process, thereby eliminating lack of control over the vertical location of the restorative components. The planar surfaces are easier to mate then conical surfaces and promote both vertical location control (reducing vertical location variability), as well as seal robustness (further amplified by the high pre-load).

The anti-rotational section 146 includes a cylindrical main body 420 having a top end coupled to the component head 402 and an opposite end that ends in a conical section 422. The cylindrical main body 420 includes an exterior surface 424 that includes circular ridges 426 and grooves 428. The circular ridges 426 interlock with the grooves 312 of the anti-rotational section 134 of the implant 102 while the grooves 428 interlock with the ridges 310 of the anti-rotational section 134.

The bottom retention engagement section 148 includes a cylindrical body 440 that has a smaller diameter than the diameter of the anti-rotational section 146. The cylindrical body 440 has an exterior surface 442 that includes threads 444. As will be explained, the threads 444 engage the threads of the retention component 104.

As shown in FIGS. 1 and 2, the retention component 104 includes a compliant conical element 150 and a cylindrical main body 152 that includes an interior bore 154 with a locking section 156 that interfaces with the head of the driver tool 108. In this example, the retention component 104 may be fabricated from SS316L stainless steel and may be treated with a lubricious surface coating such as gold-plating. The purpose of the gold-plated coating is to increase the efficiency of the retention component 106 and the resultant pre-load within the assembly for a given rotational force. In this example, the implant 102 is titanium. Of course, other dental restoration appropriate materials may be used for the components of the assembly 100.

FIG. 5A-5B shows detailed views of the retention component 104. The compliant conical element 150 includes a cylindrical exterior surface 502 and a sloped exterior surface 504 near an open end 506. A beveled interior annular surface 508 is formed on the open end 506. The beveled interior annular surface 508 is connected to a cylindrical interior surface 510. The cylindrical interior surface 510 leads to a threaded interior surface 512. The compliant conical element 150 includes four arms 522, 524, 526, and 528. Four slots 532, 534, 536, and 538 are interposed between the four arms 522, 524, 526, and 528. The four arms 522, 524, 526, and 528 each include the threaded interior surface 512.

The cylindrical main body 152, including the interior bore 154, is coupled to the locking section 156. The interior diameter of an interior space 540 of the locking section 156 is less than the diameter of the threaded interior surface 512 of the bore 154. The interior space 540 includes a series of six interior surfaces 542 that mate with the head of the driver tool 108.

The driver tool 108 includes a handle 160 attached to a shaft 162. The shaft 162 has a diameter that allows the shaft 162 to be inserted into the bore 140 of the mating component 106. The driver tool 108 includes a head 164 that has a series of surfaces that lock into the corresponding interior surfaces 542 of the interior space 430 of the locking section 156 of the retention component 104. In this example, the head 164 is a hexagonal cross-section and the locking section 156 is a hexagonal socket. Of course other shapes may be used for the interface between the head 164 and the socket.

The present system 100 primarily pertains to the retention of mating components (e.g., abutments, impression copings, cover screws, etc.) such as the mating component 106 to a dental implant such as the implant 102. The connection to the dental implant 102 via the retention component 104 allows the user to orientate or align the restorative mating component 106 to the desired position and retain the mating component 106 without the mating component 106 rotating and without the user handling an attachment component such as a screw that must be inserted in conjunction with the mating component, thereby avoiding misplacement and potentially the patient swallowing the screw. The mating component 106 is retained by the retention component 104 when the mating component 106 is assembled with the implant 102. The retention component 102 is preassembled by the manufacturer inside the dental implant 102 by collapsing the arms 522, 524, 526, and 528 of the retention component 104 to insert the retention component 104 in the retention component section 136 of the implant 102. The insertion of the dental component 106 in conjunction with the driver tool 108 allows the return of the retention component 104 to its pre-collapsed form as shown in FIG. 2.

During dental implant surgery, the dental implant 102 of the retention insert assembly 100 is placed in the patient. The retention component 104 is pre-assembled in the dental implant 102 and is therefore also placed in the patient with the implant 102. As shown in FIG. 1, the exterior sloped surface of the compliant conical element 150 of the retention component 104 is roughly the same shape of the conical middle section 322 of the implant 102. The exterior diameter of the locking section 156 of the retention component 104 is roughly the same as the diameter of the bottom section 324. Thus, the retention component 104 is initially seated on the interior bottom end 326 of the bottom section 324 of the implant 102 as shown in FIG. 1. The outer diameter of the complaint conical element 150 is slightly larger than the diameter of the interior bore 132 of the anti-rotational section 134. The arms 522, 524, 526, and 528 of the retention component 104 are pinched in to allow the insertion of the retention component 104 into the implant 102.

The mating restorative component 106 is aligned and positioned on top of the dental implant 102. The middle anti-rotational section 146 of the mating component 106 engages the anti-rotation section 134 of the implant 102. The circular ridges 310 and grooves 312 of the anti-rotation section 134 of the implant mate with the corresponding grooves 428 and ridges 426 of the anti-rotational section 146 of the mating component 106 to prevent rotational motion of the mating component 106. The retention engagement section 148 of the mating component 106 is inserted into the open end 506 of the retention component 104. The threads 444 on the exterior surface 442 of the cylindrical body 440 of the mating component 106 contact the threaded interior surface 512 of the cylindrical interior surface 510 of the retention component 104.

The driver tool 108 is inserted through the access hole 140 of the mating component 104 so the head 164 engages the driving feature (e.g., hexagonal interior surfaces 542) of the retention component 104. The retention component 104 is then rotated by the driver tool 108 and thereby engages the mating component 106. The exterior threads 444 of the mating component 106 engage the interior threads 512 of the retention component 104 by a user applying downward pressure on the mating component 106 via pushing the driver tool 108. When the driver tool 108 is turned, the retention component 104 is rotated, thus engaging the interior threads 512 with the exterior threads 444 of the mating component 106. As the driver tool 108 continues to be rotated, the motion spreads apart the arms 522, 524, 526, and 528 of the retention component 104. The retention component 104 pulls the mating component 106 apically via the engagement of the exterior threads 444 with the interior threads 512 until full mating of the mating component 106 and the implant 102. The driver tool 108 is then removed. On full mating, the tops of the arms 522, 524, 526, and 528 contact the retention stop surface 314 of the implant 102 as shown in FIG. 2. As also shown in FIG. 2, the planar stop surface 408 of the bottom rim 406 of the dental component 106 creates a seal by contacting the annular stop surface 308 of the annular interior shoulder 306 of the implant 102. Thus, the top of the arms 522, 524, 526, and 528 of the retention component 104 contacting the retention stop surface 314 of the implant 102 and the planar stop surface 408 of the mating component 106 contacting the annular stop surface 308 of the implant 102 serve to hold the now attached retention component 104 and mating component 106 to the implant 102.

Further since the retention component 104 is not contained inside the mating component 106 nor above the occlusal surface of the dental implant 102 in the assembly 100, the design flexibility of a restoration for a patient is greatly increased by allowing the possibility of an extremely short and angled restoration.

Figure 6A:
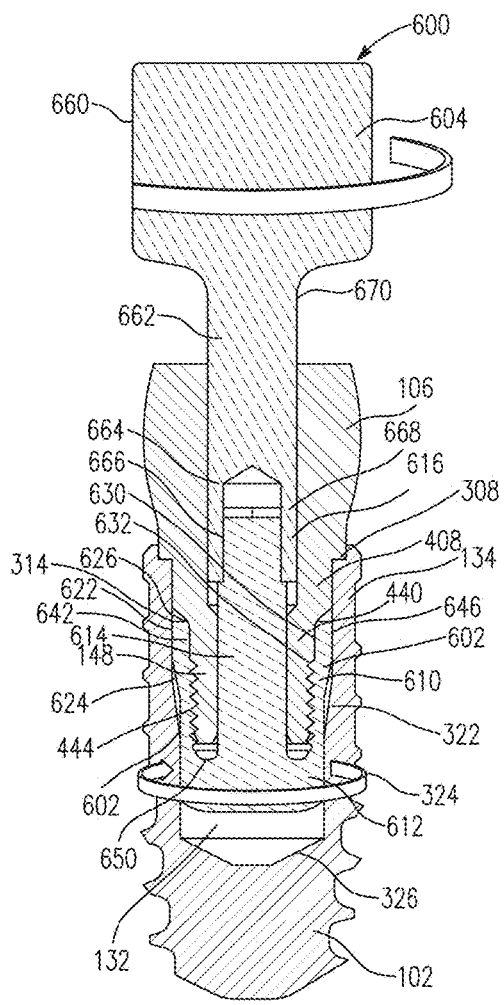
FIG. 6A is a cross-section view of an alternate interface assembly between a dental implant, retention component, and a dental component.
Figure 6B:
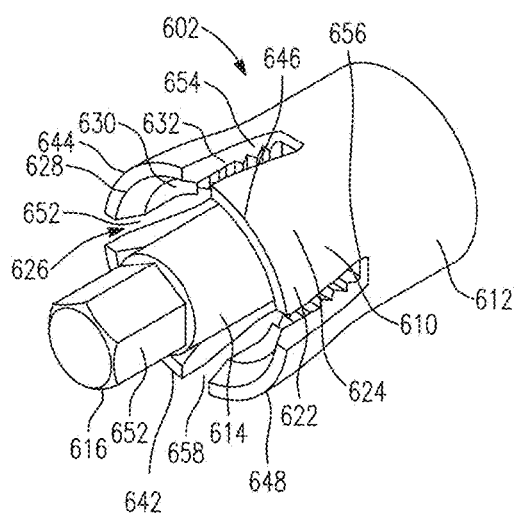
FIG. 6B is a perspective view of the retention component in FIG. 6A.
Figure 6C:
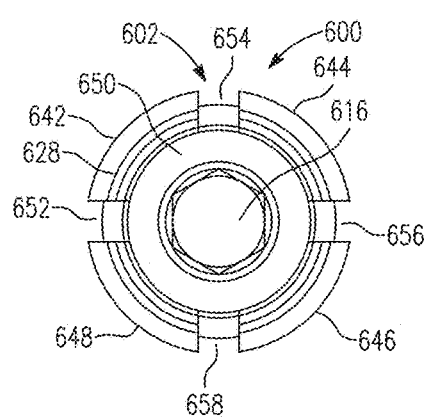
FIG. 6C is a top view of the retention component in FIG. 6A.

FIG. 6A shows an alternate dental assembly 600 including an alternate retention component 602 and an alternate driver tool 604. The dental assembly 600 includes an implant 102 and a mating component 106 that are identical to their counterparts described in FIGS. 1 and 2 above. FIG. 6B shows a perspective view of the alternate retention component 602 and FIG. 6C shows a top view of the alternate retention component 602. The alternate retention component 602 includes a compliant conical element 610, a cylindrical support body 612, a central shaft 614, and a driver engagement head 616. The driver engagement head 616 interfaces with the driver tool 604.

The compliant conical element 610 includes a cylindrical exterior surface 622 and a sloped exterior surface 624 near an open end 626. A beveled interior annular surface 628 is formed on the open end 626. The beveled interior annular surface 628 is connected to a cylindrical interior surface 630. The cylindrical interior surface 630 leads to a threaded interior surface 632. The compliant conical element 610 includes four arms 642, 644, 646, and 648. Four slots 652, 654, 656, and 658 are interposed between the four arms 642, 644, 646, and 648. The four arms 642, 644, 646, and 648 each include the threaded interior surface 632.

The cylindrical support body 612 includes a bottom surface 650 that forms an interior space in conjunction with the compliant conical element 610. The central shaft 614 is mounted on the bottom surface 650. The driver engagement head 616 includes a hexagonal shaped exterior 652 that mates with the driver tool 604. In this example, the shaft 616 is a single piece fabrication with the cylindrical support body 612 and the compliant conical section 610. In this example, the alternate retention component 602 is stainless steel with gold plating.

The driver tool 604 includes a handle 660 attached to a shaft 662. The shaft 662 has a diameter that allows the shaft 662 to be inserted into the bore 140 of the mating component 106. The driver tool 604 includes a head 664 that includes a socket 666 with hexagonal interior surfaces 668 that lock into the corresponding hexagonal surfaces 652 of the engagement head 616 of the retention component 602. The driver tool 604 includes an optional mechanical fuse section 670 that reduces the cross-section of the shaft 662 such that the torque at which it would shear would be higher than the torque required for securing the retention component 602, but lower than the torque required to destroy the retention component 602 and/or the interface between the retention component 602 and the driver tool 604. Thus, in the event of failure of the driver tool 604, the retention component 602 and the corresponding components such as the implant 102 and the mating component 106 will be protected.

During dental implant surgery, the dental implant 102 of the retention insert assembly 100 is placed in the patient. The retention component 602 is pre-assembled in the dental implant 102 and is therefore also placed in the patient. As shown in FIG. 6A, the exterior sloped surface of the compliant conical element 610 and the cylindrical support body 612 roughly match the shape of the conical middle section 322 and the bottom section 324 of the implant 102. Thus, the retention component 602 is initially seated on the interior bottom end 326 of the bottom section 324 of the implant 102. The outer diameter of the complaint conical element 610 is slightly larger than the diameter of the interior bore 132 of the anti-rotational section 134 of the implant 102. The arms 642, 644, 646, and 648 of the retention component 602 are pinched in to allow the insertion of the retention component 602 into the implant 102.

The mating component 106 is aligned and positioned on top of the dental implant 102. The middle anti-rotational section 146 of the mating component 106 engages the anti-rotation section 134 of the implant 102 and prevents rotation of the mating component 106. The retention engagement section 148 of the mating component 106 is inserted into the open end 616 of the retention component 602. The threads 444 on the exterior surface 442 of the cylindrical body 440 of the mating component 106 contact the threaded interior surface 632 of the cylindrical interior surface 630 of the retention component 602.

The driver tool 604 is inserted through the access hole 140 of the mating component 106 so the socket 666 mates with the engagement head 616 of the retention component 602. A user may push the driver tool 604 so the mating component 106 is forced downward into the implant 102. The retention insert 602 is then rotated by the driver tool 604 and engages the mating component 104. The exterior threads 444 of the mating component 106 engage the interior threads 632 of the retention component 602. When the driver tool 604 is turned, the retention component 602 is rotated, thus engaging the interior threads 632 with the exterior threads 444 of the mating component 106. As the driver tool 604 continues to be rotated, the imparted motion to the retention component 106 spreads the arms 642, 644, 646, and 648 of the retention component 602 apart. The retention component 602 pulls the mating component 106 apically via the engagement of the exterior threads 444 and interior threads 632 until full mating of the mating component 106 and the implant 102 is achieved. The driver tool 604 is then removed. On full mating, the top of the arms 642, 644, 646, and 648 contact the retention stop surface 314 of the implant 102 as shown in FIG. 6A. As also shown in FIG. 6A, the planar stop surface 408 of the dental component 106 creates a seal by contacting the annular stop surface 308 of the implant 102. Thus, the top of the arms 642, 644, 646, and 648 of the retention component 602 contacting the retention stop surface 314 of the implant 102 and the planar stop surface 408 contacting the annular stop surface 308 serve to hold the now attached retention component 602 and mating component 106 to the implant 102.

Figures 6D, 6E:
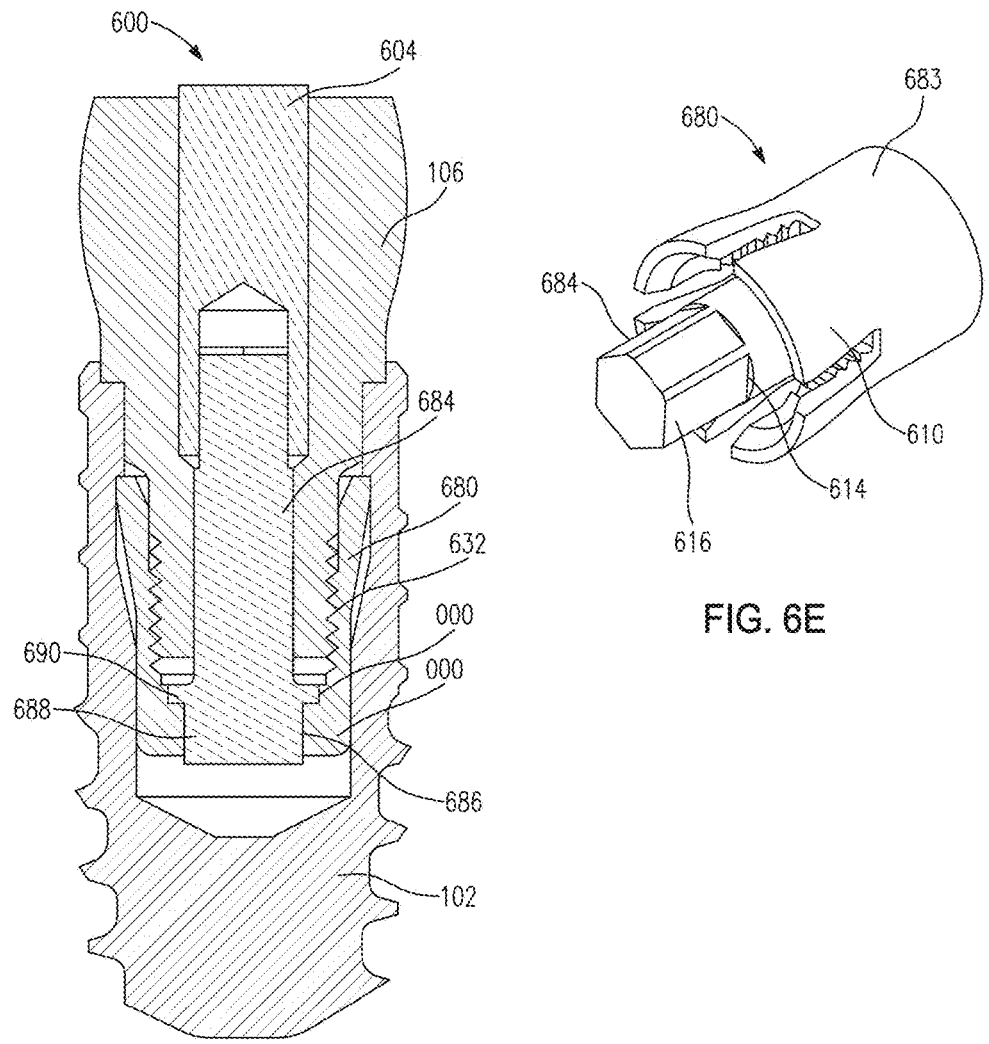
FIG. 6D is a cross-section view of the alternate interface in FIG. 6A with a two piece retention component.
FIG. 6E is a perspective view of the two piece retention component in FIG. 6E.

Alternatively, the retention component 602 may be a two-piece assembly. FIG. 6D is a cross-section view of the alternate interface assembly 600 in FIG. 6A with a two-piece retention component 680. FIG. 6E is a perspective view of the two-piece retention component 680 in FIG. 6E. The interface assembly 600 in FIG. 6D has the same implant 102, mating component 106, and driver tool 604 as those shown in FIG. 6A. The retention component 680 has the same general shape and functions the same as the retention component 602 shown in FIGS. 6A-6C above. The retention component 680 has a compliance piece 682 that includes the conical compliant section 610 and the bottom surface 650 of the retention component 602 in FIG. 6A. A separate insert 684 forms the central shaft 614 and driver engagement head 616.

As shown in FIG. 6D, the compliance piece 682 has a bottom hole 686 that holds the insert 684. The insert 684 includes a pin 688 that is inserted in the bottom hole 686. An annular protrusion 690 rests on the bottom surface 650 of the compliance piece 682. The insert 684 is locked in place by a press fit with the annular protrusion 690. Alternatively, the pin 688 may be attached via a screw to the compliance piece 682.

Figure 7A:
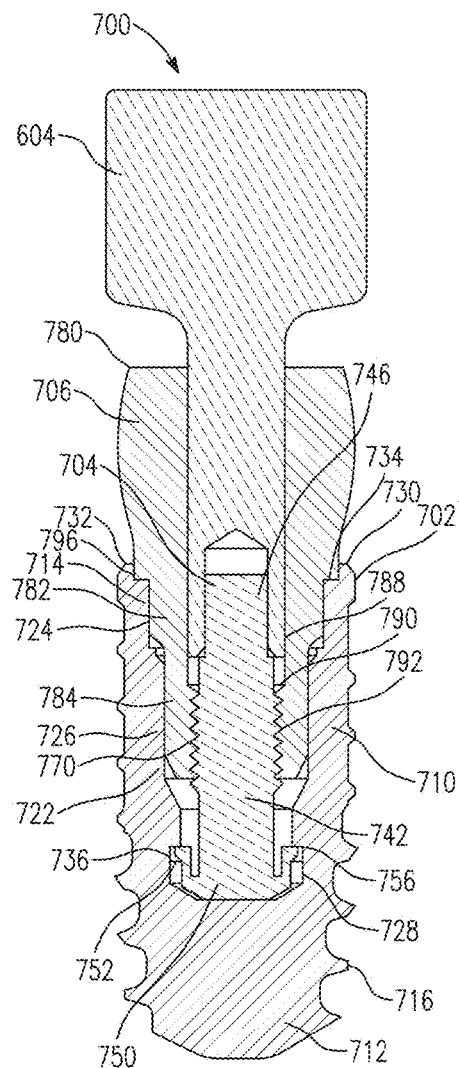
FIG. 7A is a cross-section view of an alternate interface assembly between a dental implant, a retention component, and a dental component.
Figure 7B:
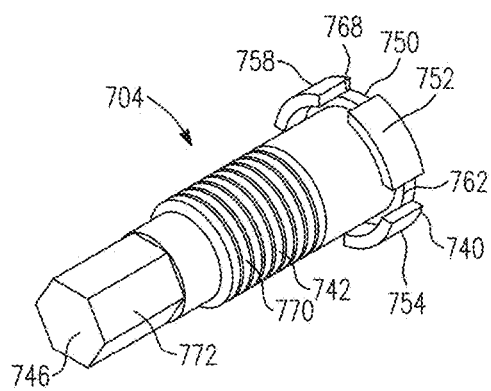
FIG. 7B is a perspective view of the retention component in FIG. 7A.
Figure 7C:
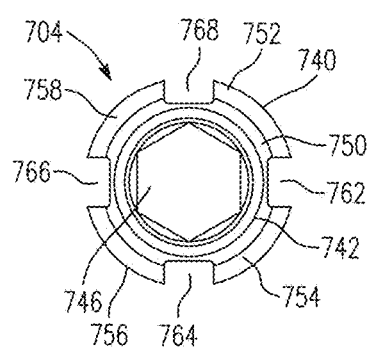
FIG. 7C is a top view of the retention component in FIG. 7A.

FIG. 7A shows an alternate dental implant assembly 700 that includes a dental component 706 that may be attached to an implant 702 via an alternate retention component 704. A driver tool 604 identical to the driver tool 604 in FIG. 6A is used in FIG. 7A to attach the components in the assembly 700. FIG. 7B shows a perspective view of an alternate retention component 704 and FIG. 7C shows a top view of the retention component 704. The implant 702 in this example includes a roughly cylindrical body 710 that includes a closed end 712 and an opposite open end 714. The cylindrical body 710 includes a series of exterior threads 716 that hold the implant 702 into the bone. The implant 702 includes an interior bore 722 having an anti-rotation section 724, a middle cylindrical chamber 726, and a retention component chamber 728.

The open end 714 includes an annular ring 730 defining an annular interior shoulder 732 that includes an annular stop surface 734. The annular stop surface 734 is substantially horizontal and allows the dental component 706 to be seated and creates a seal as will be explained below.

The anti-rotation section 724 of the implant 702 includes a set of circular ridges and grooves that mate with corresponding surfaces on the dental component 706 to prevent rotational motion of the dental component 706 when it is inserted into the dental implant 702. The retention component chamber 728 includes a retention stop wall 736 having a first diameter that is less than the diameter of the retention component chamber 728.

The alternate retention component 704 includes a compliant element 740 on one end of a cylindrical support body 742, and a driver engagement head 746 on the other end. The engagement head 746 interfaces with the driver tool 604.

The compliant element 740 includes a cylindrical bottom plate 750 that supports four compliant arms 752, 754, 756 and 758. Each of the compliant arms 752, 754, 756, and 758 are angled outward from the support body 742. The diameter of the bottom plate 750 is roughly that of the diameter of the retention stop wall 736 to allow the bottom plate 750 to be inserted through the retention stop wall 736 into the chamber 728. Four slots 762, 764, 766, and 768 are interposed between the four arms 752, 754, 756, and 758. The four arms 752, 754, 756, and 758 are approximately the same height as the retention component chamber 728 of the implant 702.

The cylindrical support body 742 includes exterior threads 770. The driver engagement head 746 includes a hexagonal shaped exterior surface 772 that mates with the driver tool 604. In this example, the alternate retention component 704 is stainless steel with gold plating.

The dental component 706 in this example includes a head 780 that is coupled to one end of a middle anti-rotational section 782. The opposite end of the middle section 782 is coupled to a retention engagement section 784. An interior bore 788 is formed through the dental component 706. The bore 788 has a diameter sufficient to accommodate the driver engagement head 746. The retention engagement section 784 has a cylindrical inner surface 790 that includes threads 792. A planar stop surface 796 is formed on the bottom of the head 780 of the dental component 706.

During dental implant surgery, the dental implant 702 of the retention insert assembly 700 is inserted in an osteotomy formed in the patient. The retention component 704 is pre-positioned in the retention chamber 728 of the dental implant 702 and is therefore also placed in the patient with the dental implant 702. The retention component 704 may be pushed into the retention component chamber 728 prior to placing the implant 702 in the patient. The insertion of the retention component 704 causes the arms 752, 754, 756, and 758 to be flexed inward by the narrower diameter of the retention component chamber 728. The arms 752, 754, 756, and 758 then expand out and contact the retention stop wall 736 of the implant 702. Thus, the bottom 750 of the retention component 704 is seated and retained in the retention component chamber 728 of the implant 702.

The mating component 706 is aligned and positioned on top of the dental implant 702. The middle anti-rotational section 782 of the mating component 706 engages the anti-rotation section 724 of the implant 702. The retention engagement section 784 of the mating component 706 is inserted around the driver engagement head 746. The threads 792 on the interior surface 790 of the retention engagement section 784 of the mating component 706 contact the threads 770 of the cylindrical body 742 of the retention component 702.

The driver tool 604 is inserted through the interior bore 794 of the mating component 706 so the socket 666 mates with the engagement head 742 of the retention component 704. The retention component 704 is then rotated by the driver tool 604 and engages the mating component 706. The user pushes the driver tool 604 downward so the interior threads 792 of the mating component 706 engage the exterior threads 770 of the retention component 704. When the driver tool 604 is turned, the retention component 704 is rotated, thus engaging the threads 770 of the retention component 704 with the interior threads 792 of the mating component 706. As the driver tool 604 continues to be rotated, the retention component 704 pulls the mating component 706 apically via the engagement of the exterior threads 770 and interior threads 792 until full mating of the mating component 706 and the implant 702 is achieved. The driver tool 704 is then removed. On full mating, the planar stop surface 794 of the dental component 706 creates a seal by contacting the annular stop surface 734 of the implant 702. Thus, the top of the arms 752, 754, 756, and 758 of the retention component 706 contacting the retention stop surface 736 of the implant 702 and the planar stop surface 794 contacting the annular stop surface 734 serve to hold the now attached retention component 704 and mating component 706 to the implant 702.

Figure 8A:
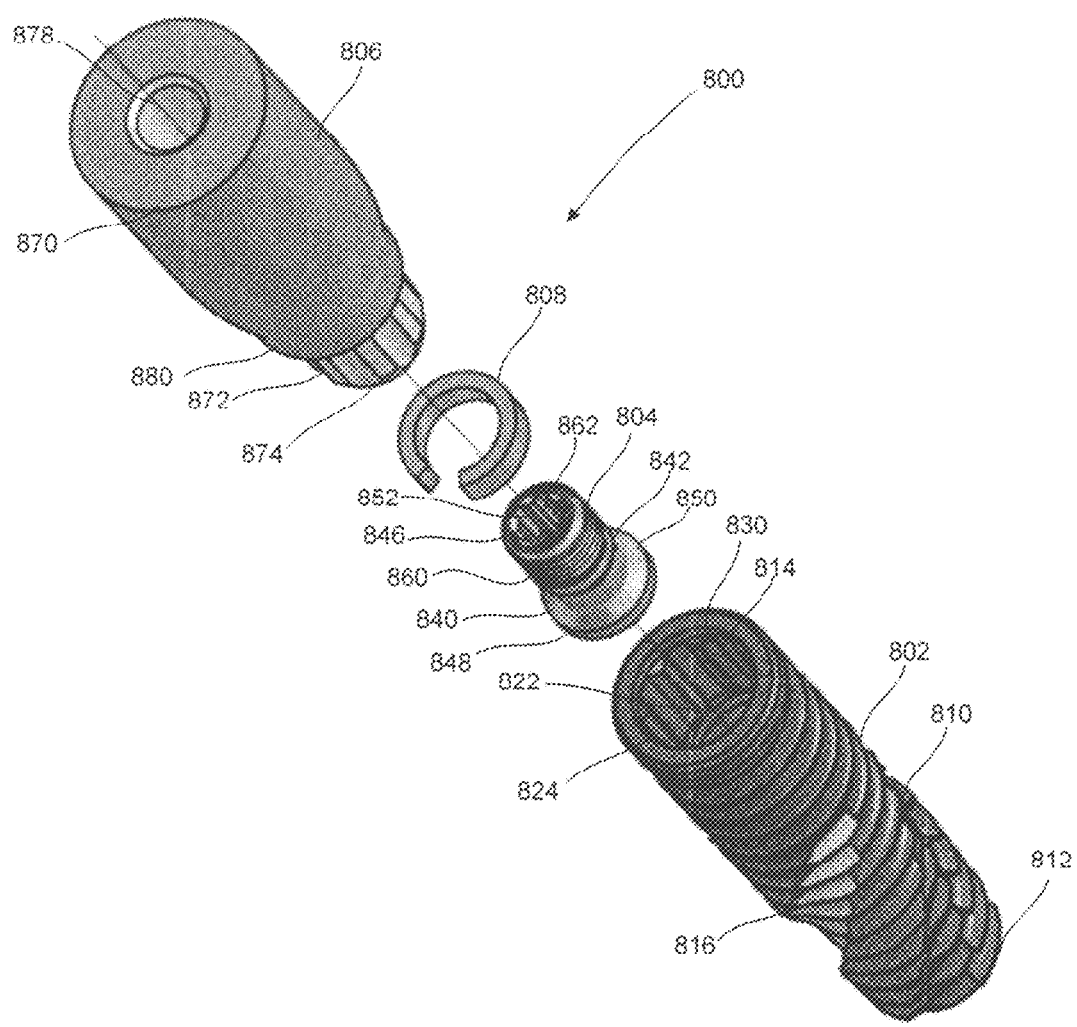
FIG. 8A is a perspective view of an alternate interface assembly between a dental implant, a retention component, a snap ring insert, and a mating component.
Figures 8B, 8C:
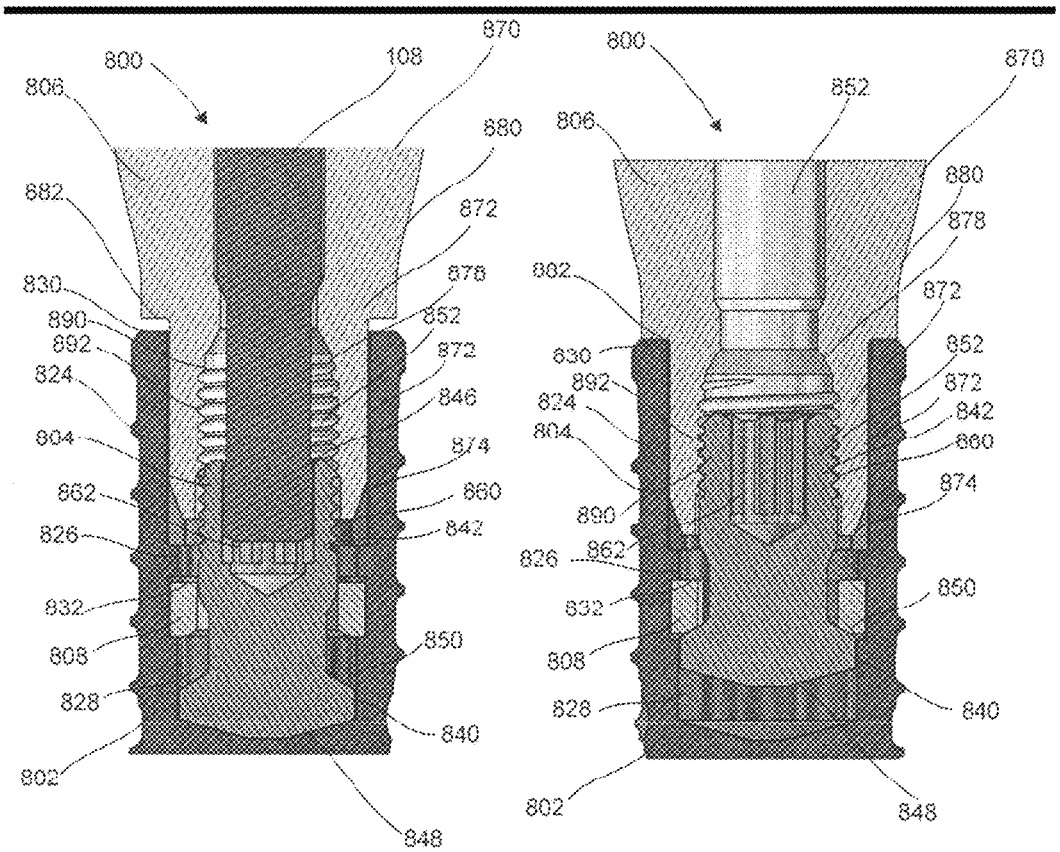
FIG. 8B is a cross-section view of the alternate interface assembly in FIG. 8A when the mating component is inserted.
FIG. 8C is a cross-section view of the alternate interface assembly in FIG. 8A when the mating component is fully mated with the dental implant using the retention component.

FIG. 8A shows a perspective view of an alternate dental implant assembly 800 that includes an implant 802 that may be attached to a dental component 806 via an alternate retention component 804 in conjunction with a C-shaped snap ring insert 808. FIG. 8B shows a side view of the components of the dental implant assembly 800 when the dental component 806 is inserted into the implant 802. FIG. 8C is a side view of the components of the dental implant assembly 800 when the dental component 806 is fully attached to the implant 802. A driver tool 108 identical to the driver tool 108 in FIG. 1 is used in FIG. 8B to attach the components.

The implant 802 in this example includes a roughly cylindrical body 810 that includes a closed end 812 and an opposite open end 814. The cylindrical body 810 includes a series of exterior threads 816 that hold the implant 802 into the bone. The implant 802 includes an interior bore 822 having an anti-rotation section 824, a middle neck section 826, and a retention component chamber 828.

The open end 814 includes an annular stop surface 830. The annular stop surface 830 is substantially horizontal and allows the dental component 806 to be seated and creates a seal as will be explained below.

The anti-rotation section 824 includes a set of circular ridges and grooves that mate with corresponding surfaces on the dental component 806 to prevent rotational motion when the dental component 806 is inserted into the dental implant 802. The retention component chamber 828 includes an annular retention stop wall 832 formed by the middle neck 826 that has a diameter that is less than the diameter of the retention component chamber 828.

Figure 9A:
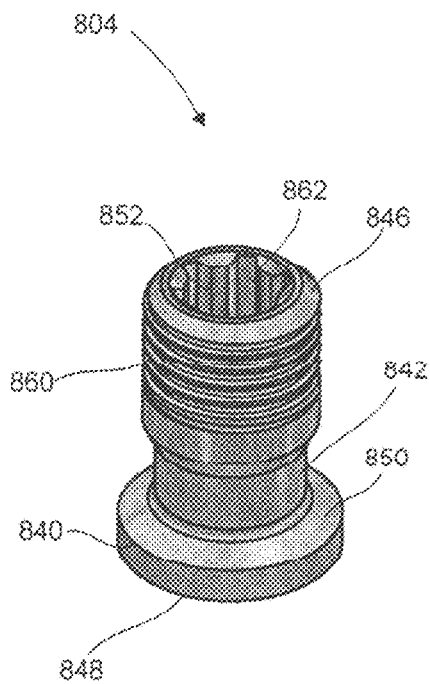
FIG. 9A is a perspective view of the retention component in FIG. 8A.
Figure 9B:
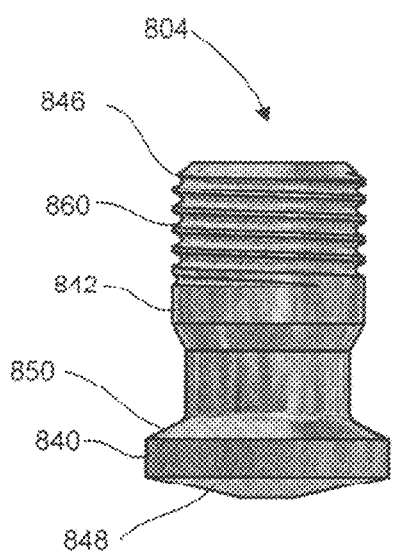
FIG. 9B is a side view of the retention component in FIG. 8A.
Figure 9C:
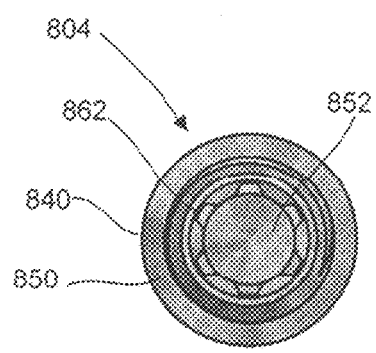
FIG. 9C is a top view of the retention component in FIG. 8A.

FIG. 9A shows a perspective view of the alternate retention component 804, FIG. 9B is a side view of the retention component 804 and FIG. 9C shows a top view of the retention component 804. The alternate retention component 804 includes an annular protrusion 840 on one end of a cylindrical support body 842, and a driver engagement head 846 on the other end. The annular protrusion 840 includes a conical bottom 848 and a circular contact surface 850. The engagement head 846 includes a socket 852 that interfaces with the driver tool 108. The diameter of the annular protrusion 840 is roughly that of the diameter of the retention stop wall 832 of the implant 802 to allow the annular protrusion 840 of the retention component 804 to be inserted in the retention chamber 828 of the implant 802. The insert 808 may be compressed to a smaller diameter fit into the retention component chamber 828. The insert 808 then expands to a greater diameter to be retained in the retention component chamber 828 by the retention stop wall 832. The snap ring insert 808 is intended to be removable should it and/or the retention component fail 806 to mitigate the osseointegrated implant 802 from having to be trephined out of a patient. The snap ring insert 808 may be removed by a specialized tool that engages optional protrusion features on the snap ring insert 808 and compressing the snap ring insert 808 to a smaller diameter to be released from the retention chamber 828 and thus removed from the implant 802.

The cylindrical support body 842 includes exterior threads 860. The socket 852 of the driver engagement head 846 includes a hexagonal shaped interior surface 862 that mates with the driver tool 108. In this example, the alternate retention component 804 is stainless steel with gold plating.

The dental component 806 in this example includes a head 870 that is coupled to a middle anti-rotational section 872 that is coupled to a retention engagement section 874. An interior bore 878 is formed through the dental component 806. The bore 878 has a diameter sufficient for the dental component 806 to accommodate the driver engagement head 846. The head 870 has a sloped bottom section 880 that terminates in an annular contact shoulder 882. The retention engagement section 874 has a cylindrical inner surface 890 that includes threads 892.

FIG. 8B is a cross-section view of the alternate interface in FIG. 8A when the dental component 806 is inserted into the implant 802 and downward pressure is exerted via the driver tool 108. During dental implant surgery, the dental implant 802 of the retention insert assembly 800 is inserted in an osteotomy created in the patient. The retention component 804 and insert 808 are pre-positioned in the retention component chamber 828 of the dental implant 802 and are therefore also placed in the patient as shown in FIG. 8B. The retention component 804 may be pushed into the retention component chamber 828 first and then the insert 808 is compressed to fit through the neck 826 into the retention component chamber 828. Once the insert 808 is placed in the chamber 828, it expands and is held in place by the retention stop wall 832.

The mating component 806 is aligned and positioned on top of the dental implant 802. The middle anti-rotational section 872 of the mating component 806 engages the anti-rotation section 824 of the implant 802 preventing the rotation of the mating component 806. The retention engagement section 874 of the mating component 806 is inserted around the driver engagement head 846. The threads 892 on the interior surface 890 of the retention engagement section 874 of the mating component 806 contact the threads 860 of the cylindrical support body 842 of the retention component 804.

The driver tool 108 is inserted through the interior bore 852 of the mating component 806 so the head mates with the engagement surface 862 of the retention component 804. The user may apply downward force via the driver tool 108 to the mating component 806 in order to engage the retention component 804. As a result, the interior threads 892 of the mating component 806 engage the exterior threads 860 of the retention component 804. When the driver tool 108 is turned, the retention component 804 is rotated, thus engaging the threads 860 with the interior threads 892 of the mating component 806. As the driver tool 108 continues to be rotated, the retention component 804 pulls the mating component 806 apically via the engagement of the exterior threads 860 and interior threads 892 until full mating of the mating component 806 and the implant 802 is achieved. The driver tool 108 is then removed.

FIG. 8C is a cross-section view of the alternate interface 800 in FIG. 8A when the dental component 806 is fully mated with the dental implant 802 and the driver tool 108 is removed. On full mating, the circular contact surface 850 of the annular protrusion 840 of the retention component 804 is compressed against one side of the insert 808. The opposite side of the insert 808 contacts the retention stop surface 832 of the implant 802. The mating component 806 is held by the interface of the threads 860 and 892 to the retention component 804. The contact surface 882 of the dental component 806 contacts the annular contact surface 830 of the implant 802 to create an additional seal.

As explained above, the mating component in the previous examples may include devices other than abutments. For example, a cover screw component 1000 shown in FIGS. 10A-10D may be used to protect the interior of the implant 802 and the retention component 804 in FIG. 8A prior to insertion of an abutment or other prosthetic later in the restorative process. FIG. 10A is a cross-section view of the assembly of the cover screw dental component 1000 with the implant 802 and retention component 804 shown in FIG. 8A-8C. FIG. 10B is a perspective, exploded view of the components of the cover screw dental component 1000, FIG. 10C is a top view of the cover screw dental component 1000, and FIG. 10D is a side view of the cover screw dental component 1000. The cover screw dental component 1000 includes a cap 1002 that is attachable to a cylindrical body 1004. The assembly of the cap 1002 and cylindrical body 1004 may be seen in FIGS. 10A and 10D.

The cap 1002 includes a top surface 1010 with a socket 1012 that includes an interface surface 1014. The socket 1012 allows the cover screw dental component 1000 to be rotated into place by a screw driver or specialized driver tool such as the driver tool 108 in FIG. 8B. An opposite bottom surface 1020 includes a protruding stem 1022. The stem 1022 includes a locking annular slot 1024 that allows the retention of the cap 1002 with the cylindrical body 1004. The stem 1022 also includes an engagement section 1026 that has exterior features 1028 that mate with the socket 852 of the engagement head 846 of the retention component 804 in FIG. 8A.

The cylindrical body 1004 includes an annular tab 1030 that locks into the annular slot 1024 of the cap 1002. The cylindrical body 1004 includes an exterior surface 1032 that includes locking features 1034 that interface with the anti-rotational section 824 of the implant 802. The cylindrical body 1004 includes an interior surface 1036 that includes threads 1038.

As may be shown in FIG. 10A, the cover screw 1000 is inserted into the implant 802 such that the locking features 1034 interface with the anti-rotational section 824 of the implant 802. The engagement section 1026 is inserted into the engagement head 852 of the retention component 804. The cap 1002 is rotated by a suitable tool inserted in the socket 1012 causing the retention component 804 to be rotated and move apically toward the cover screw 1000. The threads 1038 of the cylindrical body 1004 engage the threads 860 of the cylindrical support body 842 of the retention component 804. When fully assembled, the bottom surface 1020 creates a seal with the annular contact surface 830 of the implant 802. In this manner, the retention component 804 rotates via the rotation of the cap 1002 into the fixed cylindrical body 1004.

Figure 11A:
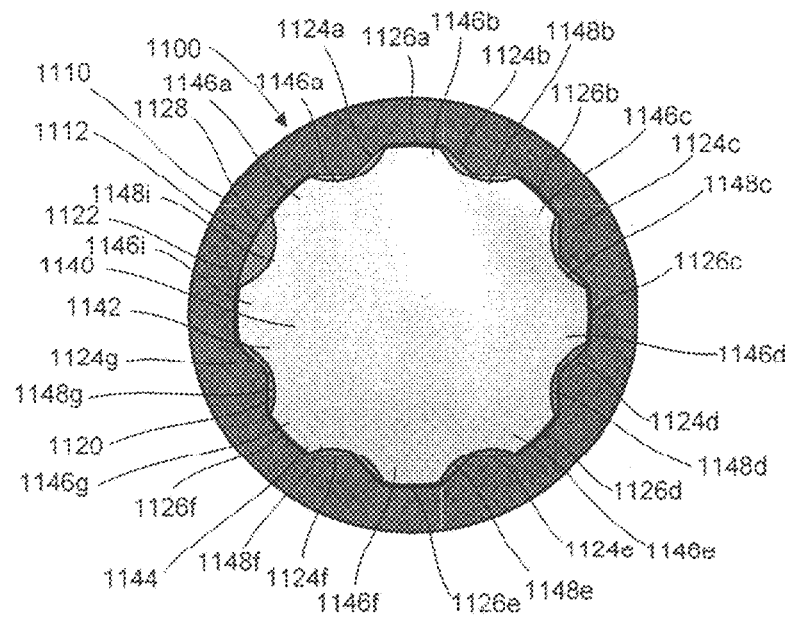
FIG. 11A is a top view of an alternate implant interface for a dental component with different rotational orientations.

FIG. 11A is a top view of an alternate implant interface 1100 for a dental component 1140 with different rotational orientations. An implant 1110 is similar to the implant 102 in FIG. 1, the implant 702 in FIG. 7A, or the implant 802 in FIG. 8A. The implant 1110 has an alternate anti-rotational section 1112 that prevents the rotation of the dental component 1120 when the dental component 1120 is inserted in the implant 1110. The anti-rotational section 1112 includes a socket 1120 that includes a cylindrical inner surface 1122 that includes seven radial protrusions 1124a-1124g. Each of the radial protrusions 1124a-1124g is equally spaced from each other, forming corresponding equally spaced and dimensioned gaps 1126a-1126f. The radial protrusions 1124a and 1124g are spaced away from each other at a greater radial distance of the circumference of the inner surface 1122 and form a larger circular gap 1126.

The dental component 1140 includes an anti-rotational section 1142 that has a cylindrical exterior surface 1144. The cylindrical exterior surface 1144 includes eight symmetrical radial tabs 1146a-1146i that form corresponding grooves 1148a-1148i. When the dental component 1140 is inserted into the implant 1110, the radial tabs 1146a-1146i are inserted into the gaps 1126a-1126f and 1128 of the implant 1110 as shown in FIG. 11A. The interaction between the tabs 1146a-1146i and the gaps 1126a-1126f and 1128 as well as the grooves 1148a-1148i and the protrusions 1124a-g prevent rotation of the dental component 1140. As shown in FIG. 11A, the larger circular gap 1128 holds two of the tabs 1146a-1146b of the dental component 1140. In this manner, the dental component 1140 may have eight separate rotational orientations relative to the implant 1110.

Figure 11B:
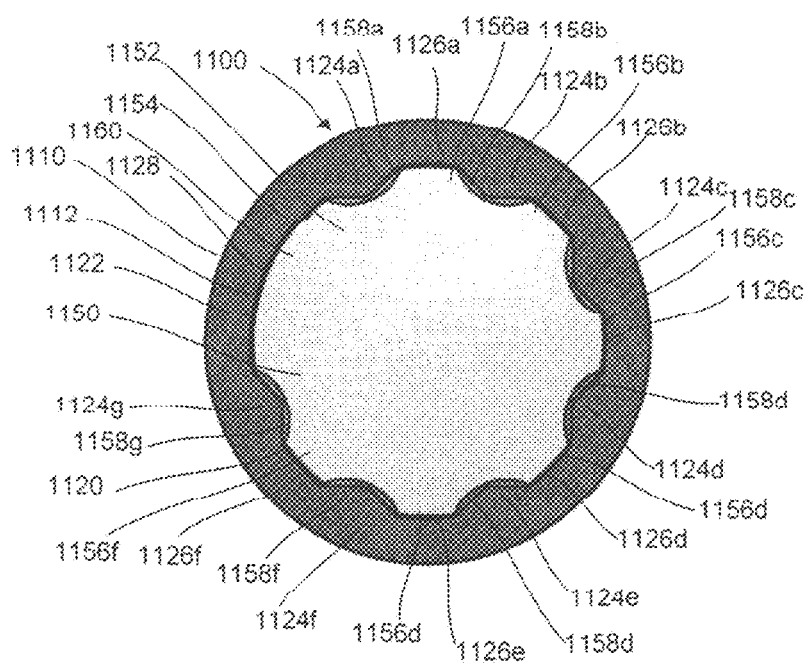
FIG. 11B is a top view of an alternate implant interface for a dental component with a specific rotational orientation.

FIG. 11B is a top view of the alternate implant interface 1100 including the implant 1110 with a dental component 1150 with a specific rotational orientation. The dental component 1150 includes an anti-rotational section 1152 that has a cylindrical exterior surface 1154. The cylindrical exterior surface 1154 includes six symmetrical radial tabs 1156a-1156f that form corresponding grooves 1158a-1158g. A larger tab 1160 is formed in one specific part of the surface 1154 between the grooves 1158a and 1158g. When the dental component 1150 is inserted into the implant 1110, the radial tabs 1156a-1156f are inserted into the corresponding gaps 1126a-1126f of the implant 1110 as shown in FIG. 11B. The larger tab 1160 is only insertable into the larger gap 1128 of the implant 1110. In this manner, the interaction between the tabs 1156a-1156f and the corresponding gaps 1126a-1126f as well as the grooves 1158a-1158g and the protrusions 1124a-g prevent rotation of the dental component 1140. As shown in FIG. 11B, the larger circular gap 1128 holds the larger tab 1160 and thereby locks the dental component 1150 in one specific rotational orientation relative to the implant 1110.

Figure 12A:
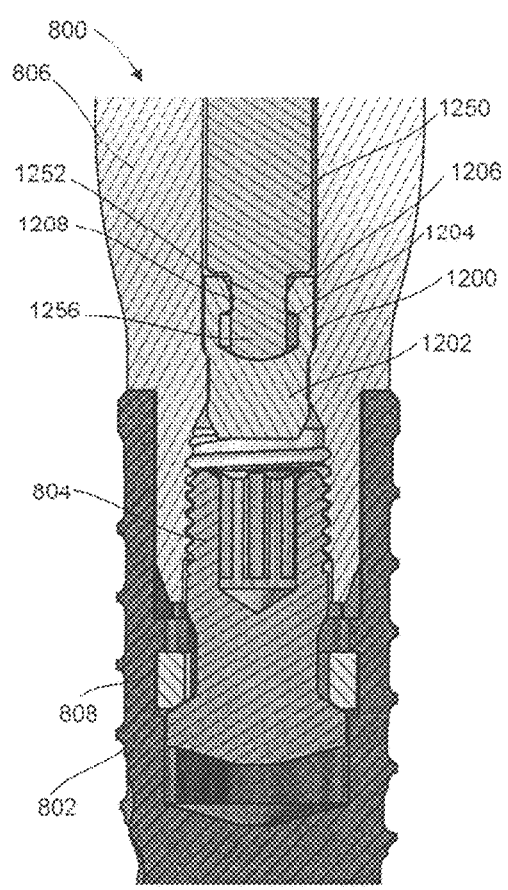
FIG. 12A is a cross section view of the interface assembly in FIG. 8A with a plug device inserted in the dental component by a plug tool.

FIG. 12A is a cross section view of the interface assembly in FIG. 8A with a plug device 1200 inserted in the dental component 806 when assembled with the implant 802 in FIG. 8B. The plug 1200 is inserted into the interior bore 878 of the dental component 806. The plug 1200 prevents debris from entering into the interior of the implant 802 and the retention component 804 before a crown or other prosthetic is installed on the dental component 806. The plug 1200 may be fabricated from silicone or any other suitable compliant material. The plug 1200 includes a main body 1202 that has a diameter that is the size of the bore 878. The plug 1200 includes a socket 1204 that includes an annular lip 1206 with a lateral slot 1208.

Figure 12B:
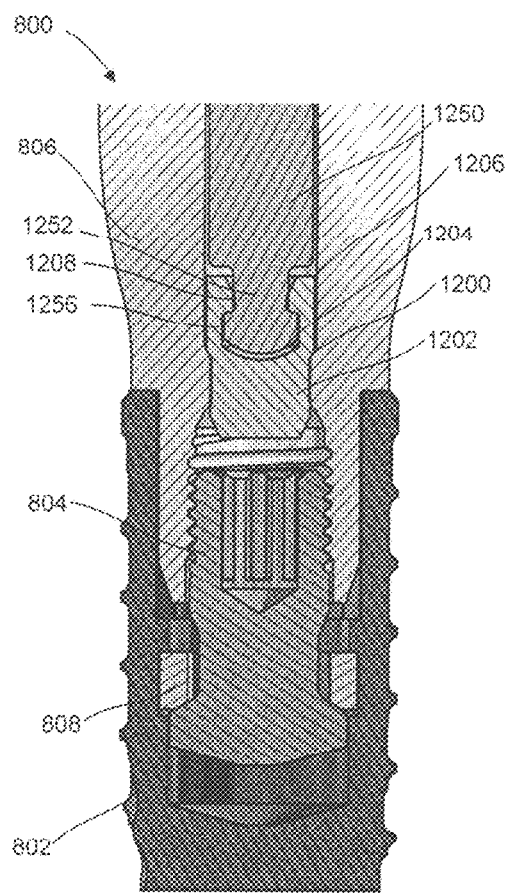
FIG. 12B is a cross section view of the interface assembly in FIG. 8A with the plug tool oriented for removing the plug device from the dental component.

A plug tool 1250 includes a head 1252 that may be inserted in the socket 1204 of the plug 1200. The head 1252 includes a tab 1256 that may be inserted through the slot 1208 in the annular lip 1206. As shown in FIG. 12A, when the tab 1206 is twisted and oriented with the slot 1208, the plug tool 1250 may be removed from the plug 1200. As shown in FIG. 12B, when the tab 1256 is inserted into the slot 1208 and the plug tool 1250 is turned, the tab 1256 contacts the annular lip 1206 and the plug tool 1250 is attached to the plug 1200. Thus, the plug 1200 may be inserted by the plug tool 1250. The plug tool 1250 is twisted, allowing the tab 1256 to be removed through the slot 1208. When the plug 1200 has to be removed, the plug tool 1250 is inserted such that the tab 1256 is inserted through the slot 1208. The plug tool 1250 is then twisted allowing the tab 1256 to contact the annular lip 1206. The plug tool 1250 may then lift the plug 1200 out of the dental component 806.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A dental restoration system comprising:
    a driver tool including a driving head;
    an implant having a tip, a cylindrical body and an open end having an annular shoulder, the cylindrical body including a retention component chamber having a retention component wall;
    a retention component seated in the retention component chamber of the implant, the retention component including a driver section for interfacing with the driving head of the driver tool and a dental component engagement section with a threaded surface, wherein the threaded surface is an interior surface of the retention component;
    a dental component including a retention component interface surface with threads and a bore therethrough, wherein the threads on the retention component interface is an external surface of the dental component; and
    wherein the dental component engages the retention component via the threaded surface of the dental component engagement section interlocks with the threads of the retention component interface surface when the dental component is inserted in the implant, the driving head of the driver tool engaging the driver section of the retention component to allow rotation of the retention component via the driver tool to engage the dental component apically such that the retention component moves, relative to the implant, in a coronal direction toward the annular shoulder as the dental component moves, relative to the implant, in an apical direction toward the tip, the retention component contacting the retention component wall and the dental component contacting the annular shoulder of the open end of the implant when the dental component is fully attached to the implant.

2. The system of claim 1, wherein the dental component is an abutment having a stem.

3. The system of claim 1, wherein the dental component is a cover screw.

4. The system of claim 1, wherein the dental component is an impression coping.

5. The system of claim 1, wherein the dental component is an attachment member which when scanned provides data relating to the implant.

6. The system of claim 1, wherein the retention component is fabricated from stainless steel with a treated lubricious surface coating and the implant is fabricated from commercially pure titanium.

7. The system of claim 6, wherein the lubricious surface coating is gold plating.

8. The system of claim 1 wherein the dental component engagement section of retention component is a female component and the threaded surface is the interior surface and wherein the retention component interface surface of the dental component is the exterior surface.

9. The system of claim 1, wherein the retention component includes compliant arms that may be compressed to fit into the retention component chamber and decompressed to contact the retention component wall.

10. The system of claim 1, wherein the driving head of the driver tool is a male component and the driver section of the retention component is a mating female component.

11. The system of claim 1 wherein the driving head of the driver tool is a female component and the driver section of the retention component is a mating male component.

12. The system of claim 1, wherein the dental component includes an anti-rotational section and wherein the implant includes an anti-rotational section, wherein the anti-rotation section of the dental component interfaces with the anti-rotational section of the implant to prevent rotation of the dental component.

13. The system of claim 12, wherein the anti-rotational section of the dental component fixes a rotational orientation of the dental component relative to the implant in one specific rotational orientation.

14. A dental restoration system comprising:
a driver tool including a driving head;
an implant having a tip, a cylindrical body and an open end having an annular shoulder, the cylindrical body including a retention component chamber having a retention component wall, and a retention stop surface;
a retention component seated in the retention component chamber of the implant, the retention component including a driver section for interfacing with the driving head of the driver tool and a dental component engagement section with a threaded surface and a plurality of compliant arms that may be compressed to fit into the retention component chamber and decompressed to contact the retention component wall; and
a dental component including a retention component interface surface with threads and a bore therethrough,
wherein the dental component engages the retention component via the threaded surface of the dental component interlocking with the threads of the retention component interface surface when the dental component is inserted in the implant, the driving head of the driver tool engages the driver section of the retention component to allow rotation of the retention component via the driver tool to engage the dental component apically such that the retention component moves, relative to the implant, in a coronal direction toward the annular shoulder until a top surface of the plurality of compliant arms contacts the retention stop surface and the dental component moves, relative to the implant, in an apical direction toward the tip until the dental component contacts the annular shoulder of the open end of the implant when the dental component is fully attached to the implant.

* * * * *